United States Patent
Sipple

(10) Patent No.: US 10,470,712 B2
(45) Date of Patent: Nov. 12, 2019

(54) BIOMARKER DETECTION AND IDENTIFICATION SYSTEM AND APPARATUS

(71) Applicant: Daniel Sipple, St. Paul, MN (US)

(72) Inventor: Daniel Sipple, St. Paul, MN (US)

(73) Assignee: Sipple Medical, LLC, Saint Paul, MN (US)

( * ) Notice: Subject to any disclaimer, the term of this patent is extended or adjusted under 35 U.S.C. 154(b) by 156 days.

(21) Appl. No.: 15/319,770

(22) PCT Filed: Jun. 19, 2015

(86) PCT No.: PCT/US2015/036830
§ 371 (c)(1),
(2) Date: Dec. 17, 2016

(87) PCT Pub. No.: WO2015/196172
PCT Pub. Date: Dec. 23, 2015

(65) Prior Publication Data
US 2017/0172507 A1    Jun. 22, 2017

Related U.S. Application Data

(60) Provisional application No. 62/014,513, filed on Jun. 19, 2014.

(51) Int. Cl.
*A61B 5/00* (2006.01)
(52) U.S. Cl.
CPC ............ *A61B 5/6848* (2013.01); *A61B 5/686* (2013.01); *A61B 5/6852* (2013.01); *A61B 5/7405* (2013.01); *A61B 2505/05* (2013.01)

(58) Field of Classification Search
CPC . A61B 17/3401; A61B 5/6848; A61B 5/6858; A61B 17/3403; A61M 5/46
(Continued)

(56) References Cited

U.S. PATENT DOCUMENTS

| 4,435,037 A | 3/1984 | Abramson et al. |
| 4,564,011 A | 1/1986 | Goldman |

(Continued)

FOREIGN PATENT DOCUMENTS

| CN | 201361376 Y | 12/2009 |
| CN | 101710074 A | 5/2010 |

(Continued)

OTHER PUBLICATIONS

"Single Mode Fiber Distance, Diameter, Speed, Bandwidth Basis" published at FS.com on Sep. 8, 2012 (Year: 2012).*

(Continued)

*Primary Examiner* — Gary Jackson
*Assistant Examiner* — Zahed Kabir
(74) *Attorney, Agent, or Firm* — Grumbles Law, PLLC; Brittany R. Nanzig; Stephen F. Wolf

(57) ABSTRACT

A biomarker detector used to detect and notify a user of a biological substance. More specifically, a biomarker detector coating layered on a surgical instrument that enables a user of the surgical instrument to know when a critical bodily fluid, such as cerebrospinal fluid, or critical tissue, such as nerve tissue, has been reached by the surgical instrument, thereby allowing the user to react accordingly and avoid iatrogenic injury.

9 Claims, 8 Drawing Sheets

(58) Field of Classification Search
USPC .................. 604/506, 272, 164.01, 174, 158;
600/300; 606/246
See application file for complete search history.

(56) References Cited

U.S. PATENT DOCUMENTS

| | | | |
|---|---|---|---|
| 4,588,256 | A | 5/1986 | Onstott et al. |
| 4,589,404 | A | 5/1986 | Barath et al. |
| 4,681,398 | A | 7/1987 | Bailey et al. |
| 4,682,848 | A | 7/1987 | Cairns et al. |
| 4,754,328 | A | 6/1988 | Barath et al. |
| 5,178,153 | A | 1/1993 | Einzig |
| 5,251,276 | A | 10/1993 | Berkey et al. |
| 5,312,374 | A * | 5/1994 | Gurmarnik ............. A61M 5/46 604/117 |
| 5,405,474 | A | 4/1995 | Berkey et al. |
| 5,938,595 | A * | 8/1999 | Glass .................... G01N 33/86 356/39 |
| 6,231,568 | B1 | 5/2001 | Loeb et al. |
| 6,277,082 | B1 | 8/2001 | Gambale |
| 6,325,883 | B1 | 12/2001 | Backer et al. |
| 6,331,178 | B1 | 12/2001 | Loeb et al. |
| 6,357,447 | B1 | 3/2002 | Swanson et al. |
| 6,514,277 | B1 | 2/2003 | Lilge et al. |
| 6,551,302 | B1 | 4/2003 | Rosinko |
| 6,554,794 | B1 | 4/2003 | Mueller |
| 6,564,087 | B1 | 5/2003 | Pitris et al. |
| 6,993,376 | B2 | 1/2006 | Testardi |
| 7,022,109 | B1 * | 4/2006 | Ditto .................. A61B 17/3401 604/158 |
| 7,189,226 | B2 | 3/2007 | Auld et al. |
| 7,524,316 | B2 | 4/2009 | Hennings et al. |
| 8,235,602 | B2 | 8/2012 | Rohlen |
| 2001/0023346 | A1 | 9/2001 | Loeb |
| 2002/0037149 | A1 | 3/2002 | Chen |
| 2003/0114842 | A1 | 6/2003 | Distefano |
| 2003/0163016 | A1 | 8/2003 | Testardi et al. |
| 2004/0010204 | A1 * | 1/2004 | Weber ................ A61B 5/0084 600/547 |
| 2004/0019280 | A1 | 1/2004 | Waner |
| 2004/0086230 | A1 | 5/2004 | Lewandowski et al. |
| 2005/0004453 | A1 | 1/2005 | Tearney |
| 2005/0033389 | A1 | 2/2005 | Auld |
| 2006/0200121 | A1 * | 9/2006 | Mowery ............ A61B 18/1477 606/41 |
| 2006/0241503 | A1 | 10/2006 | Schmitt et al. |
| 2007/0065481 | A1 * | 3/2007 | Chudzik ............... A61K 9/0024 424/426 |
| 2007/0148782 | A1 | 6/2007 | Pawliszyn |
| 2007/0255264 | A1 | 11/2007 | Hickingbotham |
| 2007/0270788 | A1 | 11/2007 | Nahen et al. |
| 2008/0009751 | A1 | 1/2008 | Berndt |
| 2008/0021527 | A1 | 1/2008 | Hennings et al. |
| 2008/0287916 | A1 | 11/2008 | Agmon |
| 2011/0092823 | A1 * | 4/2011 | Tearney ............... A61B 5/0066 600/476 |
| 2011/0136132 | A1 * | 6/2011 | Tseng ................ A61B 5/14528 435/7.1 |
| 2011/0184350 | A1 * | 7/2011 | McKay ................... A61M 5/46 604/174 |
| 2011/0306854 | A1 | 12/2011 | Arnold et al. |
| 2013/0345527 | A1 | 12/2013 | Ozdil et al. |
| 2014/0378905 | A1 * | 12/2014 | Senatore ............. A61M 5/3293 604/167.02 |
| 2015/0057530 | A1 | 2/2015 | Roggeveen et al. |

FOREIGN PATENT DOCUMENTS

| | | |
|---|---|---|
| CN | 102445411 B | 10/2013 |
| EP | 1884211 A2 | 2/2008 |

OTHER PUBLICATIONS

PCT International Application Serial No. PCT/US15/36830, filed Jun. 19, 2015.
International Search Report and Written Opinion for International Application No. PCT/US2015/036830, dated Sep. 23, 2015; date of filing: Jun. 19, 2015; 5 pages.
Supplementary Search Report and Search Opinion for European Application No. 15810409.1; dated Jan. 22, 2018; date of filing: Jun. 19, 2015; 6 pages.

* cited by examiner

BIOMARKER DETECTION AND IDENTIFICATION SYSTEM AND APPARATUS

CROSS-REFERENCE TO RELATED APPLICATIONS

This application claims the benefit of U.S. Provisional Application No. 62/014,513, filed Jun. 19, 2014, titled BIOMARKER DETECTION AND IDENTIFICATION SYSTEM AND APPARATUS.

FIELD OF THE DISCLOSURE

The disclosed invention relates to a biomarker detector used to detect and identify a biological substance. More specifically, the biomarker detector can be coated on a needle to enable a user of the coated needle to detect a bodily fluid when the needle is inserted into a patient.

BACKGROUND OF THE INVENTION

Efforts to improve surgical outcomes and cost structure, particularly with spinal surgery, have led to increased use of minimally invasive procedures. These procedures often use image-guided modalities such as fluoroscopy, CT, nerve stimulators, and, more recently, the Doppler ultrasound test. While often involving less risk than surgery, minimally invasive spinal procedures, pain management procedures, nerve blocks, ultrasound guided interventions, biopsy, and percutaneous placement or open intra-operative placement continue to carry risks of ineffective outcome and iatrogenic injuries, such as infection, stroke, paralysis and death due to penetration of various structures including, but not limited to, organs, soft tissues, vascular structures, and neural tissue such as, catastrophically, the spinal cord. Injuries can occur regardless of practitioner experience because a surgical instrument must proceed through several layers of bodily tissues and fluids to reach the desired space in the spinal canal.

To illustrate, the intrathecal (or subarachnoid) space of the spinal region, where many medications are administered, houses nerve roots and cerebrospinal fluid (CSF) and lays between two of the three membranes that envelope the central nervous system. The outermost membrane of the central nervous system is the dura mater, the second is the arachnoid mater, and the third, and innermost membrane, is the pia mater. The intrathecal space is in between the arachnoid mater and the pia mater. To get to this area, a surgical instrument must first get through skin layers, fat layers, the interspinal ligament, the ligamentum flavum, the epidural space, the dura mater, the subdural space, and the intrathecal space. Additionally, in the case of a needle used to administer medication, the entire needle opening must be within the subarachnoid space.

Because of the complexities involved in inserting a surgical instrument into the intrathecal space, penetration of the spinal cord and neural tissue is a known complication of minimally invasive spine procedures and spine surgery. Additionally, some procedures require the use of larger surgical instruments. For example, spinal cord stimulation, a form of minimally invasive spinal procedure wherein small wire leads are inserted in the spinal epidural space, requires that a 14-gauge needle be introduced into the epidural space in order to thread the stimulator lead. Needles of this gauge are technically more difficult to control, posing a higher risk of morbidity. Complications can include dural tear, spinal fluid leak, epidural vein rupture with subsequent hematoma, and direct penetration of the spinal cord or nerves with resultant paralysis. These and other high-risk situations, such as spinal interventions and radiofrequency ablation, occur when a practitioner is unable to detect placement of the needle or surgical apparatus tip in critical anatomic structures.

At present, detection of such structures is operator dependent, wherein operators utilize tactile feel, contrast agents, anatomical landmark palpation and visualization under image-guided modalities. The safety of patients is reliant upon the training and experience of the practitioner in tactile feel and interpretation of the imagery. Even though additional training and experience may help a practitioner, iatrogenic injury can occur independently of practitioner experience and skill because of anatomic variability, which can arise naturally or from repeat procedures in the form of scar tissue. Fellowship training in some procedures, such as radiofrequency ablation, is not sufficiently rigorous to ensure competence; even with training, outcomes from the procedure are considerably variable. In the case of epidural injections and spinal surgery, variability in the thickness of the ligamentum flavum, width of the epidural space, dural ectasia, epidural lipomatosis, dural septum, and scar tissue all add challenges to traditional verification methods even for highly experienced operators. Additionally, repeat radiofrequency procedures done when nerves regenerate, often a year or more later, are often less effective and more difficult because the nerves' distribution after regeneration creates additional anatomic variability.

No device exists that provides objective, reliable, consistent, real-time feedback of critical tissues and bodily fluids. Further, even the concept of objective device feedback has not been accepted by proceduralists, even though millions of spinal procedures are performed annually as standard of care throughout the world.

SUMMARY OF THE INVENTION

Disclosed is a biomarker detector that can both detect and identify at least one biological substance, such as bodily fluid or tissue. In some embodiments, the biomarker detector can detect two or more biological substances and accurately indicate which biological substance is being detected. The detector, operable by a person or a machine, can be used on humans or animals and is capable of continuous or intermittent detection. For example, a needle and stylet coated with a biomarker detector coating are able to detect, in real procedural time, bodily fluids, including, but not limited to, blood, cerebrospinal fluid, and nerve tissue.

DETAILED DESCRIPTION

Figure 1:
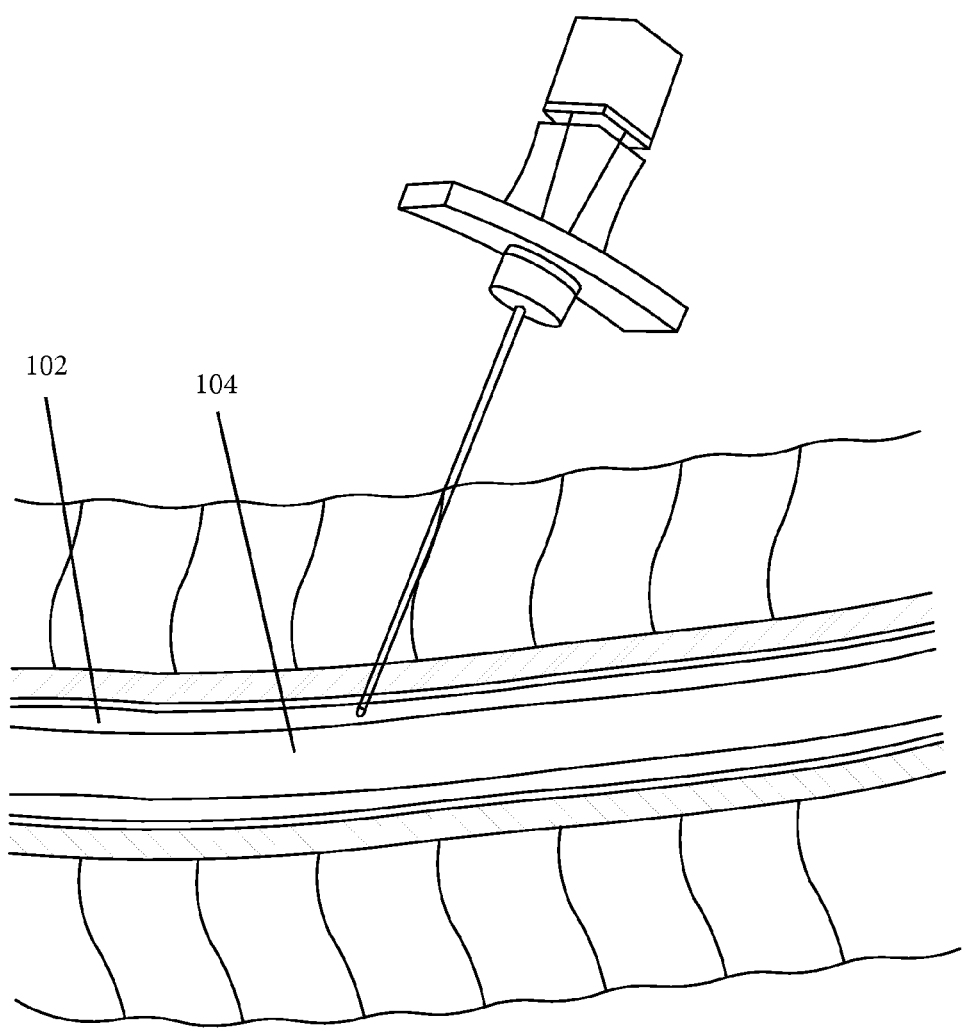
FIG. 1 illustrates an example of the disclosed invention in use.

The present disclosure relates to a biomarker detector that is used to detect biological substances, such as bodily fluids and tissues. Various embodiments of the biomarker detector will be described in detail with reference to the drawings, wherein like reference numerals represent like parts and assemblies throughout the several views. Reference to various embodiments does not limit the scope of the biomarker detector disclosed herein. Additionally, any examples set forth in this specification are not intended to be limiting and merely set forth some of the many possible embodiments for the biomarker detector. It is understood that various omissions and substitutions of equivalents are contemplated as circumstances may suggest or render expedient, but these are intended to cover applications or embodiments without departing from the spirit or scope of the disclosure. Also, it is to be understood that the phraseology and terminology used herein are for the purpose of description and should not be regarded as limiting.

Figure 3:
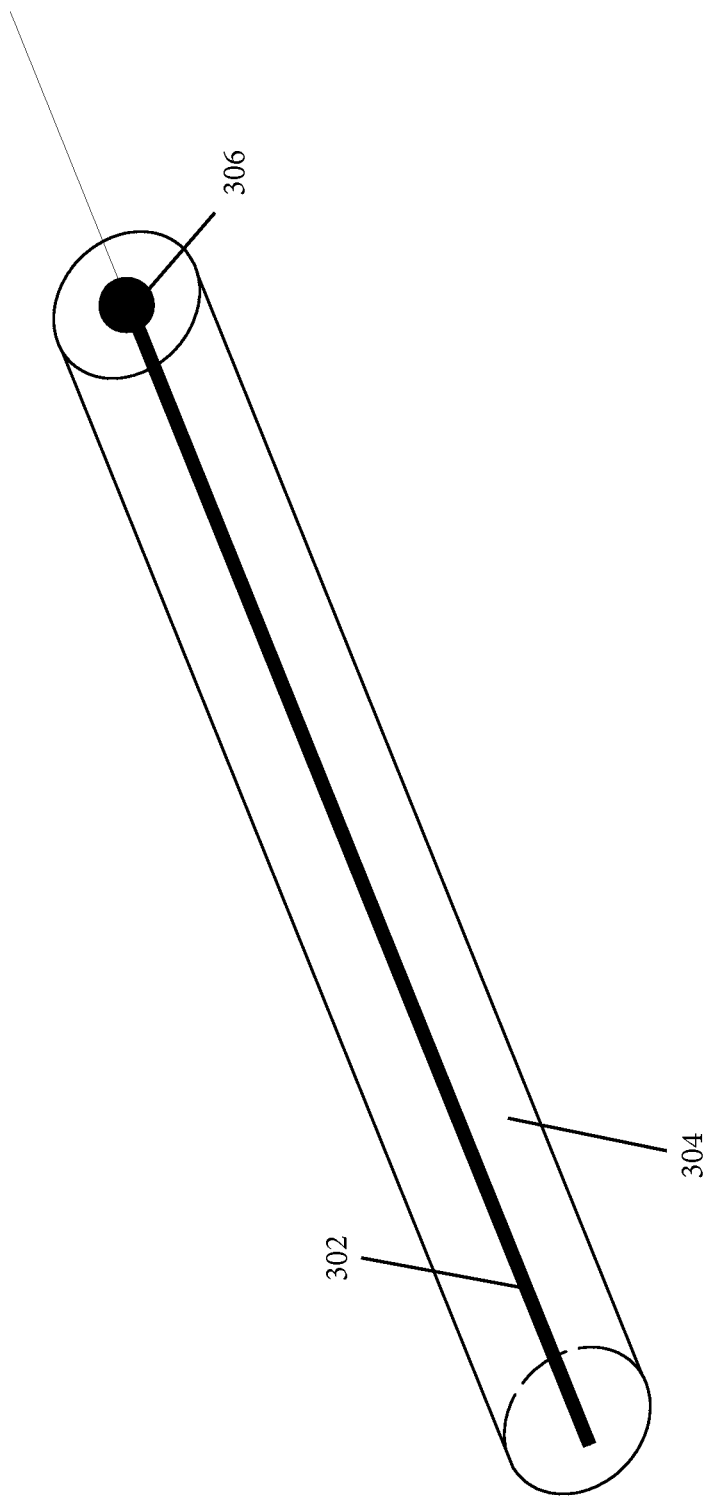
FIG. 3 illustrates an example of the disclosed invention.
Figure 4:
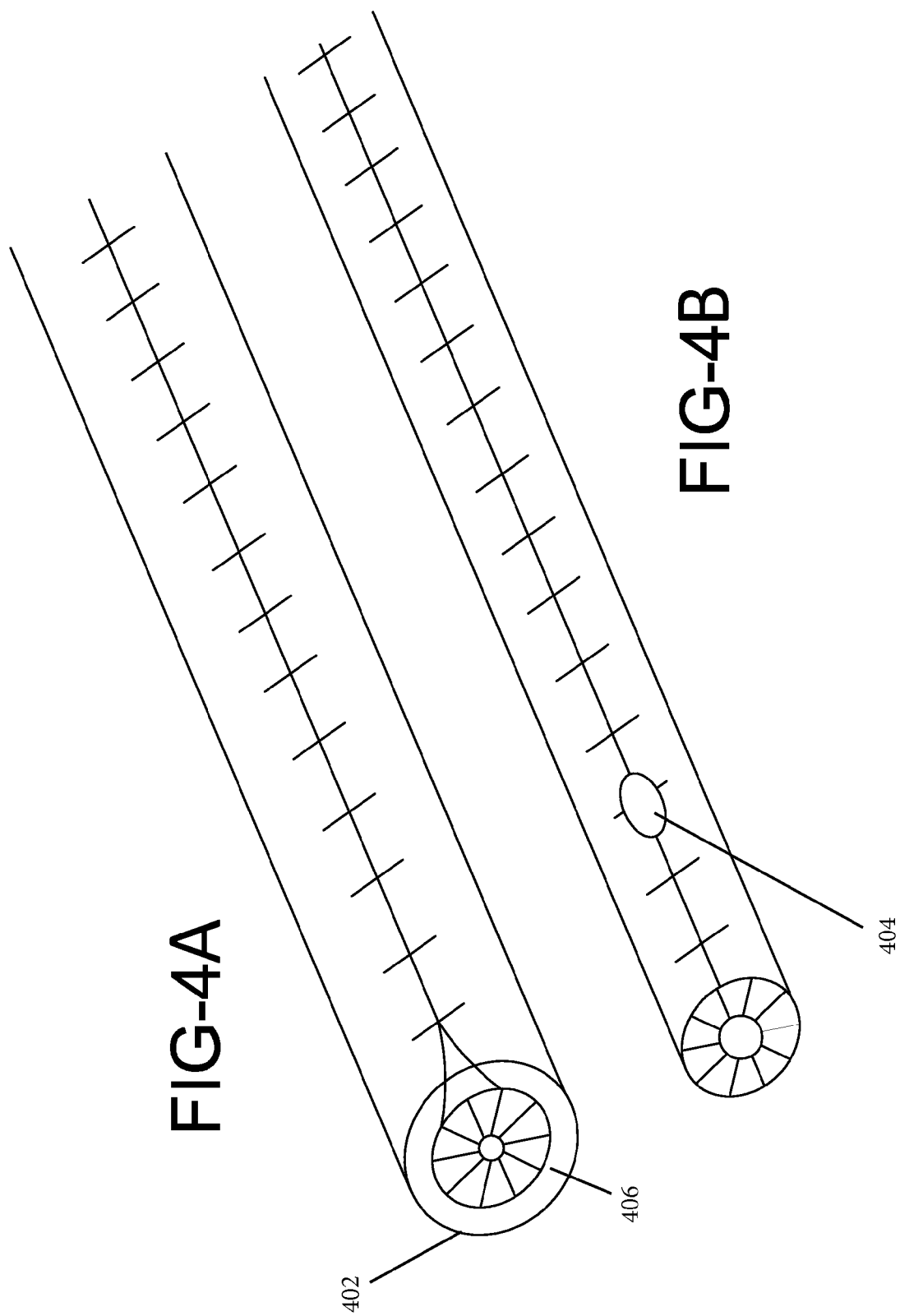
FIG. 4A illustrates an example of the disclosed invention.
FIG. 4B illustrates an example of the disclosed invention.

In one embodiment, the biomarker detector is a coating placed on a procedural or treatment instrument or apparatus, such as, but not limited to, a needle, scalpel, BOVIE® device, pacemaker, electrode, intravascular catheter, intraluminal catheter, port, sheath, and implantable pump. FIG. 3 illustrates a stylet 302 inside a needle 304 coated with the biomarker detector coating, wherein the indicator 306 is visible to an operator. FIGS. 4A and 4B illustrate a coated needle and stylet, wherein FIG. 4A shows a needle with a removable diaphragm cover 402 that covers the indicator 404 and an exposed cutting surface of the needle 406, and FIG. 4B shows the needle with diaphragm cover removed and the indicator 404 exposed.

In one embodiment, a medical instrument has a biomarker detector coating on all, some, or just the tip of the medical instrument that is either continuously or intermittently exposed pending the application. The biomarker detector can indicate detection of a biological substance by conveying a confirmatory signal such as, but not limited to, a visual or audio signal.

In one embodiment, the coating on a needle has a chemically-sensitive surface. The surface can be sensitive to various bodily fluids and tissues. It can react to those fluids and tissues similar to how litmus paper reacts to different pH levels.

For example, a needle with the biomarker detector coating can be used in conjunction with ultrasound, wherein the color of the needle or separate device may change depending on the fluid or tissue. For example, the needle or separate device may be visible on an MRI and, as it gets closer to the spine, it may darken. This can occur because the interaction between the coating and the fluids and tissues it touches can cause different types or intensities of reactions. It can react to give a darker color with fluids and tissues closer to the spine and react to give a lighter color with fluids and tissues further from the spine, or vice versa. Therefore, a needle or separate device in contact with the epidural space will appear lighter on an MRI scan than one in contact with the intrathecal space. The signal can be sent from the penetrated aspect of the apparatus, through a lumen, channel, conduit, electric conduction, or coating to the unexposed aspect of the apparatus.

In another embodiment, the biomarker detector could be a separate device that is sent with the needle. In some embodiment, it can be attached to the outer surface of the needle. In another embodiment, it can be carried inside of a catheter and exposed to fluids and tissues upon action of a user. In yet a further embodiment, it can be a separate component that is not attached to the needle, but is guided by it.

In one embodiment, the coating on a needle or separate device conveys a confirmatory signal of only one type of bodily fluid or tissue. Therefore, different coatings would be used depending on the region of the spine a user wanted to identify. For example, if the user wanted access to the intrathecal space, the user would need a coating that would only signal upon reaching the intrathecal space and would not signal when it proceeds through the outer, epidural space.

In another embodiment, the same coating on a needle or separate device can convey a confirmatory signal for various types of bodily fluids or tissues the needle or separate device is interacting with. For example, the needle or separate device, if equipped with audio signal capabilities such as a beep, can give an audible signal when it interacts with various bodily fluids and tissues. To differentiate between the varying tissues and fluids, it can give beeps with shorter intervals if it is exposed to bodily fluids and tissues closer to the spine. Therefore, the length of time between beeps when the epidural space is reached will be longer than the length of time between beeps when the intrathecal space is reached. In another example, the coated needle or separate device can have a light-producing mechanism that is activated when the coating reacts to a specific type of tissue or fluid.

In another embodiment, the coating on the needle or separate device may have a coating that detects many types of tissues and fluids by the way the tissue or fluid reacts to light. For example, the needle or separate device, with a coating or a coated tip, can have a light-producing mechanism that the coated tip reacts to or reads. The light producing mechanism can be activated upon the user's initiation and can be a light given off by a flashlight on the needle itself or it can be a separate, secondary piece of equipment that is inserted into a body in a coordinated location. The tip can react to, or read, the light as it bounces off of surrounding fluids or tissues. Depending on the wavelength of the light as it bounces off of the tissue or fluid and to the coated tip, the detector can determine what type of tissue or fluid it is in contact with or in proximity to. Upon detection of the light, the tip can electronically send the reading to a computing and display system for the user to read. The computing and display system can be a separate device or it can be contained within the needle itself.

Similarly, in another embodiment, a needle or separate device can put off sound waves that bounce off of surrounding structures. Based on the type of surrounding tissue or fluid, the sound wave profile will change, and the detector can identify, based on the wave profile, the nature of the surrounding tissue or fluid. As the needle or separate device progresses through various tissues and fluids, the profile of the sound waves will change. A computing system can match the sound waves' profile to an existing profile coordinated with a specific tissue or fluid and can indicate to the user what the tissue or fluid is.

Detection of the desired tissue or fluid can occur with minimal to no interruption to the operator, which greatly enhances the safety profile of an extensive variety of medical procedures routinely performed with these instruments and other devices. The detector can be used for minimally invasive spinal procedures as well as in multiple other medical disciplines.

The detector may confer a therapeutic benefit by verifying one or more bodily fluids and tissue types to aid in the reduction of iatrogenic injury and more precise placement.

Figure 7:
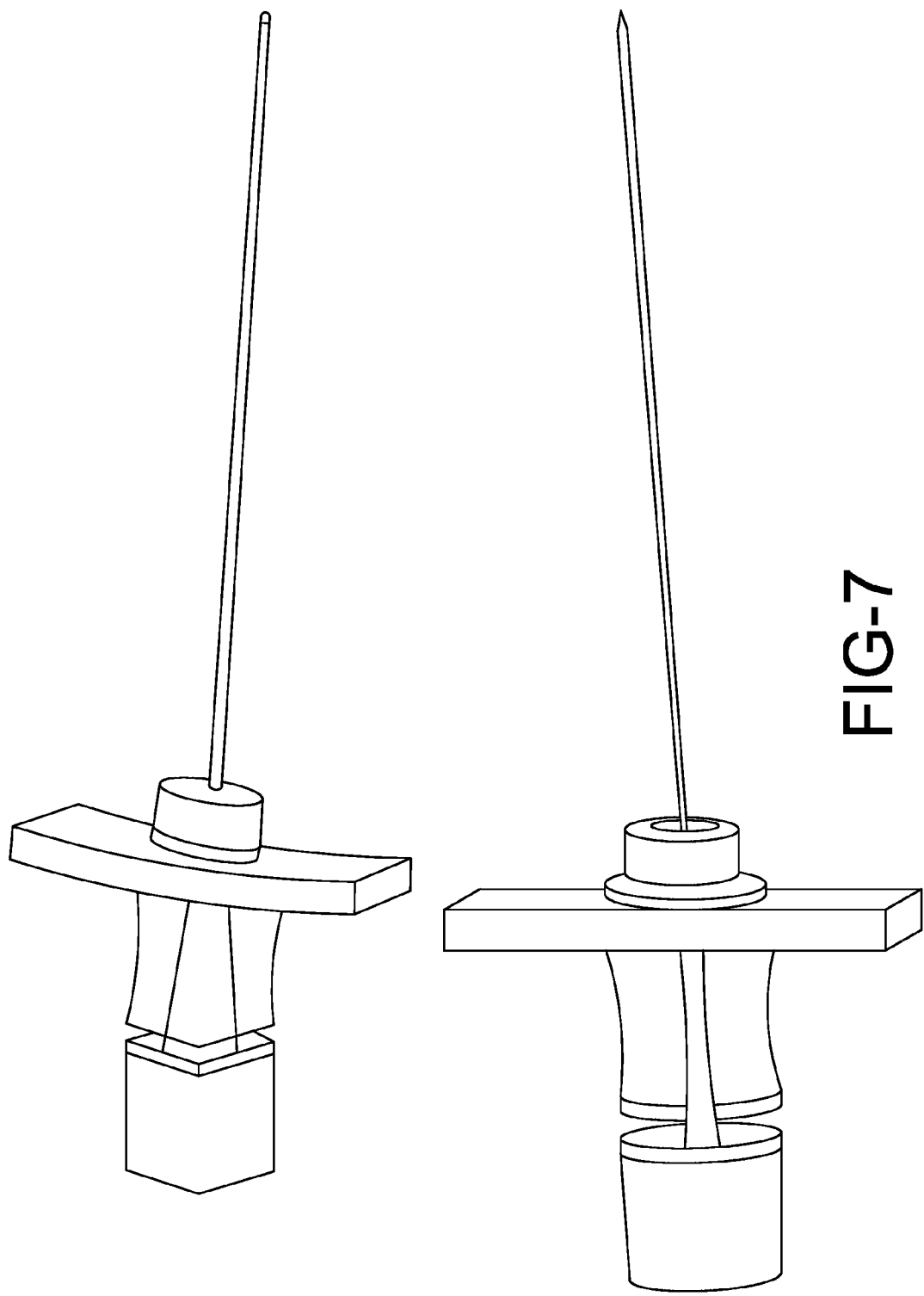
FIG. 7 shows example needles currently used for a spinal procedure.
Figure 8:
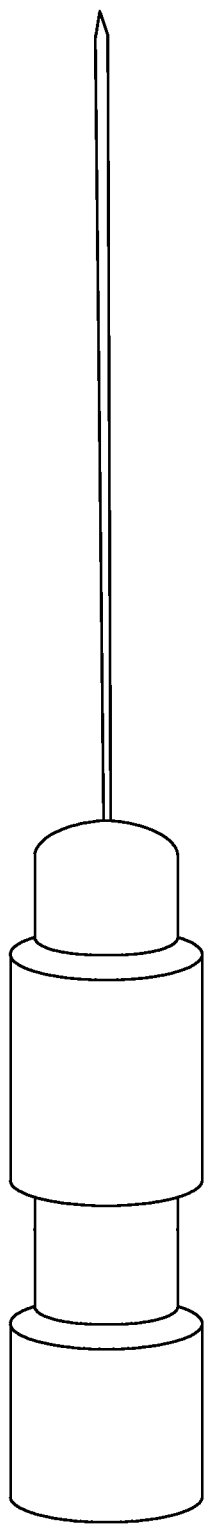
FIG. 8 shows an example of a needle currently used for a spinal procedure.

For example, when a practitioner is conducting a procedure, such as an interlaminar injection, on a patient's spine, an instrument, such as a needle, will traverse through the CSF 102 before reaching the spinal cord 104, as illustrated in FIG. 1. If the CSF 102 can be detected via the needle and stylet instrument, or catheter with obturator instrument, when either instrument is coated with the biomarker detector coating and the biomarker detector coating can provide notification of this detection, the notification may help reduce iatrogenic injury by informing the practitioner that he or she is getting close to the spinal cord. FIGS. 7 and 8 illustrate typical needles used for injection into or near the spine that can be coated with the biomarker detector coating.

Figure 2:
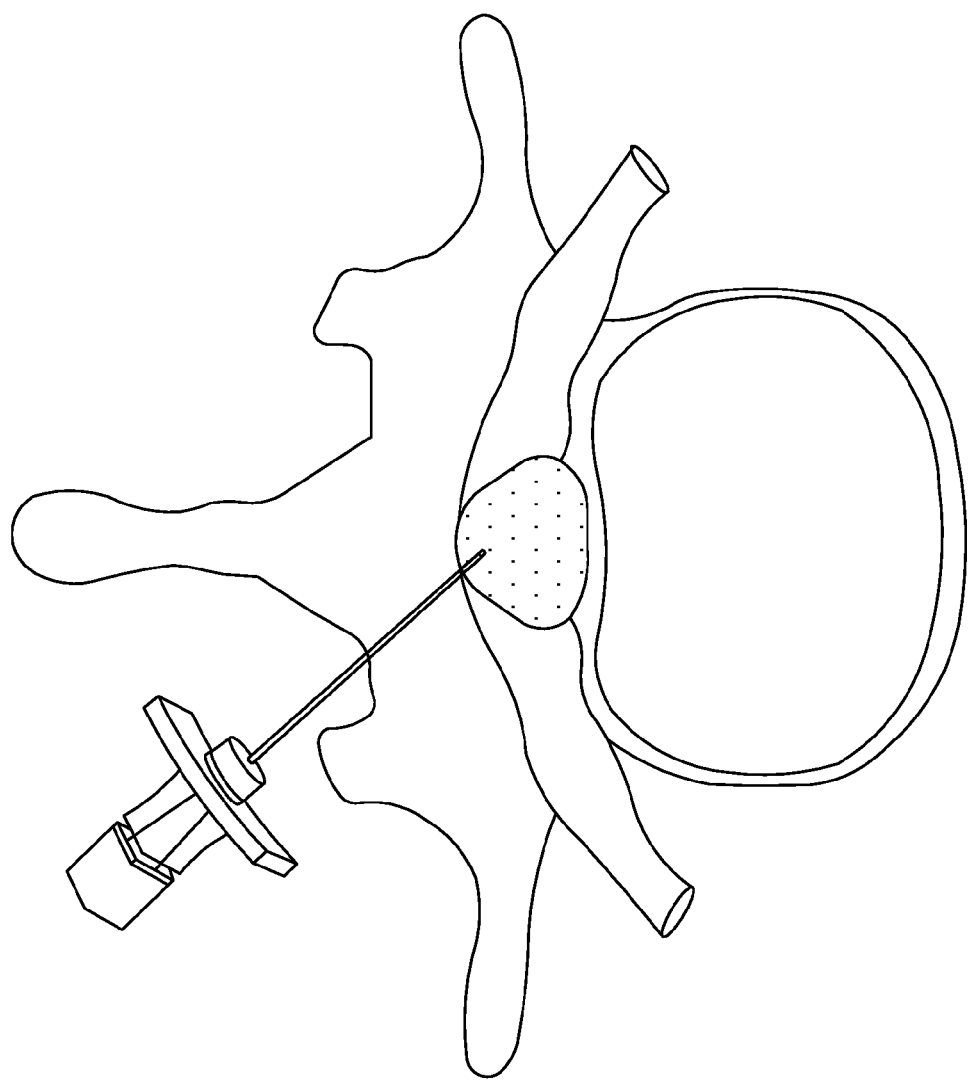
FIG. 2 illustrates an example of the disclosed invention in use.
Figure 5:
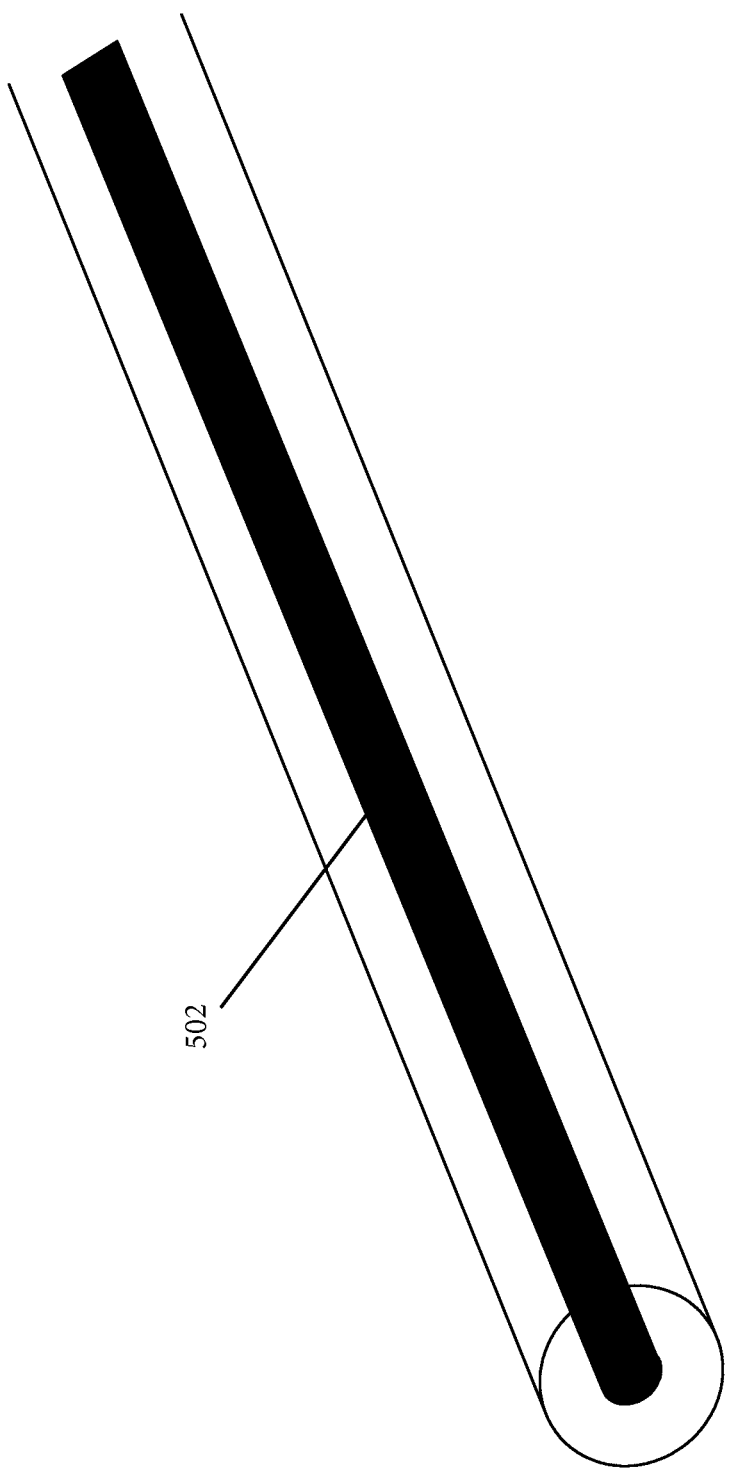
FIG. 5 illustrates an example of the disclosed invention.
Figure 6:
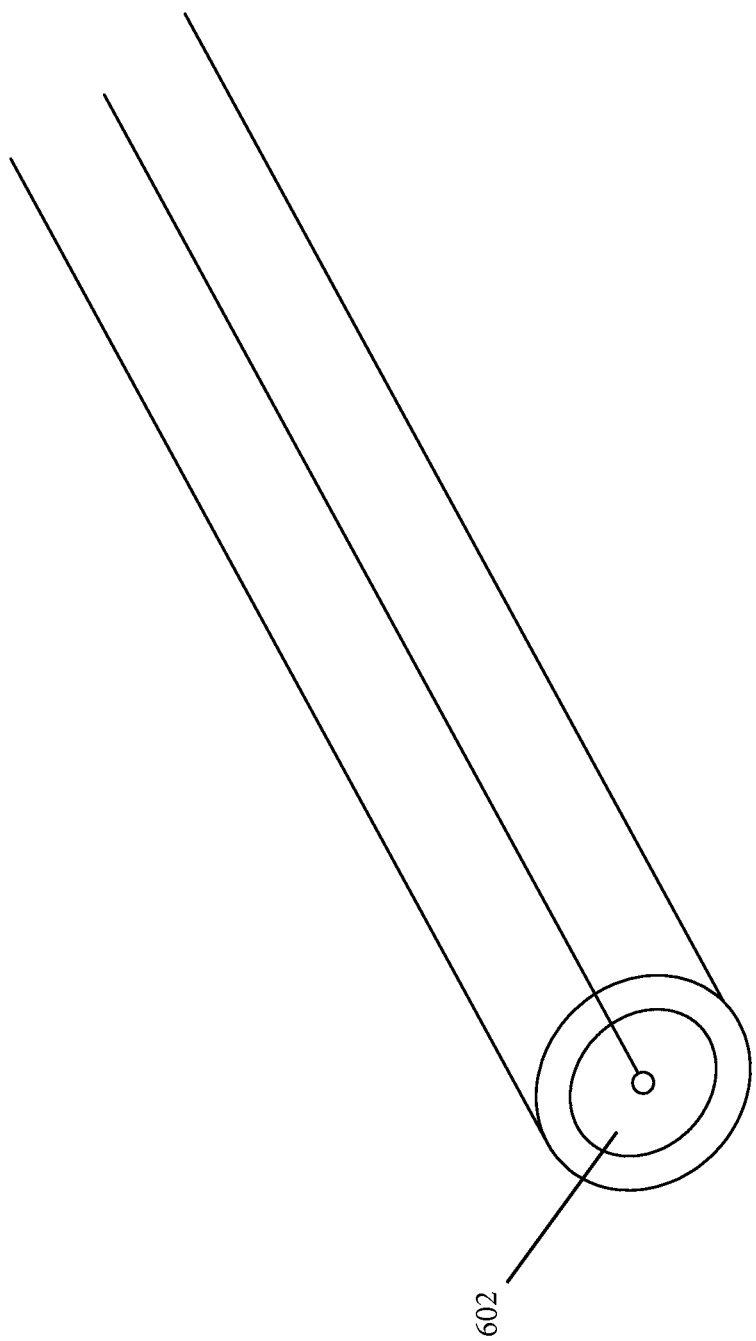
FIG. 6 illustrates an example of the disclosed invention.

The biomarker detector can serve as a protective warning system, informing the surgeon, proceduralist, or machine of the real time location of the instrument by indicating the presence of a specific biological substance using an indicator system. The indicator system can alert the practitioner if the instrument contacts CSF, blood, a nerve, or other tissue when the instrument is used for a transforaminal injection, as illustrated in FIG. 2. This alert adds a margin of safety for patients and providers alike. Regardless of whether the biological substance is bone, blood, nerve, cartilage, ligament, malignancy, or an organ, the apparatus's feedback facilitates precision in placement and increased safety. FIG. 5 illustrates one embodiment of the disclosed device wherein a stylet 502 acts as an indicator. FIG. 6 illustrates one embodiment of the disclosed device wherein an indicator 602 is on a removable diaphragm, or, alternatively, the diaphragm protects the indicator 602 until the user desires confirmation.

In one embodiment, the detection system is a robotic or other automated system that is monitored by a person. In another embodiment, the detection system is human-operated and involves no machines in the operation of the device. In some embodiments, the signal, whether auditory or visual, can be a relative or absolute signal. For example, the signal can provide absolute values of measurements taken of the type of fluid or tissue the coating is surrounded by. Alternatively, it can indicate values that are different, such as greater or smaller, than prior values when the coating moves from one type of fluid or tissue to another type.

Intentional spinal vascular access for stem cell and medication therapy has never before been pursued. Additionally, for decades, injections while on anti-coagulation were an absolute contraindication. New evidence exists that supports the idea that remaining on anticoagulation has a low risk of complication and offers protection from thrombosis. This evidence opens the door to intentional spinal vascular access for these therapies. Currently, the use of anticoagulation during lumbar transforaminal epidural steroid injections is performed on a case-by-case basis, depending on the unique risks of each patient. Fortunately, in the event of inadvertent injection of steroid into the spinal vasculature, remaining on anti-coagulation lowers the risk of spinal arterial occlusion. Dexamethasone, a non-aggregating, non-particulate steroid with a diameter of 0.5 micrometers, is exponentially smaller than red blood cells and also lowers the probability of spinal arterial occlusion. The disclosed invention could aid in further progressing intentional spinal vascular injections.

Given the concern of spinal arterial occlusion and the potential catastrophic side effects of paralysis, direct spinal radicular artery injection of steroids remains taboo, and is not pursued intentionally, even though intrathecal administration of steroids has been pursued, with significant therapeutic effect, for profoundly painful conditions such as post-herpetic neuralgia. Further, intrathecal opiate administration is accepted. Opiates, like steroids, have lipophilic characteristics, which vary from substance to substance. The relative potency of opiates as an analgesic for spinal pain increases exponentially the closer it is administered to the spinal cord. Oral, epidural, and intrathecal dosing vary in analgesic potency by factors of 1, 10 and 100, respectively. Therefore, extrapolating this trend to the spinal vasculature offers a potency factor of 1000 times higher than oral administration. Additionally, vascular uptake seen in interventional spinal procedures, while technically a reason to terminate the procedure, is pursued with dexamethasone given its safety profile with profound analgesic effect.

Direct administration of pharmacologic agents into the spinal circulation while the patient is anti-coagulated would offer a new generation of analgesia given new evidence (a) that remaining on anti-coagulation for epidural steroid injections is permissible, (b) that dexamethasone is shown not to occlude arterial circulation, and (c) that the relative potency of lipophilic medications increases exponentially the closer it comes into contact with the spinal cord. The 1000 times higher potency afforded by direct spinal arterial injection can allow microscopic amounts of medication to be introduced.

Using microscopic amounts of medication has several benefits. For decades, oral and intravenous steroids have been administered to acute spinal cord injury patients to reduce the secondary cascade of pathophysiologic mechanisms, which include inflammatory response, ischemia, lipid peroxidation, apoptosis, fluid and electrolyte disturbances, and production of free radicals, which produce a glial scar, a barrier to regeneration. Yet, their potency is exponentially lower, with greater side effects such as infection risk due to immunosuppression in the pediatric population compared to epidural, intrathecal, or radicular artery administration. Direct spinal arterial injection could allow less medication to be used and result in higher efficacy as well as fewer side effects.

While spinal interventions, injections, and surgery have many associated risks, confirmation of nerve and bone tissue using the disclosed biomarker detector offers improved efficacy for these scenarios. Being able to differentiate lumbar disc annulus fibrosis and nucleus pulposis tissue can increase the precision of lumbar discography, lumbar percutaneous disc decompression, and intradiscal stem cell therapy.

Detection of various tissue and fluid types in contact with the coated needle and stylet lowers the probability of catastrophic complication by informing the provider and or machine when critical structures, including blood and CSF, have been contacted by the needle, allowing the provider to have real time feedback, and give pause before further advancing the needle. Identical safety advantages apply in cervical and thoracic interlaminar epidural steroid injections, epidural anesthesia and catheter placement and spinal taps.

Many medical conditions can benefit from this new technology. For example, the implications for diseases with inflammation of, or trauma to, the spinal cord given this new technology are profound. Administration of at least epidural, if not intrathecal or spinal radicular artery steroid, has substantial potential to reduce secondary pathology due to spinal cord injury.

Additionally, patients suffering from degenerative neurologic conditions of the central nervous system, including multiple sclerosis, in acute flairs, similarly are grounds for study, as the degree of potency of spinal steroid administration has the capacity to arrest flairs and decelerate the pace of relapsing remitting disease. Intra-spinal administration of anti-inflammatory agents offers reduced side effect profile, opportunity for greater compliance, and again, the capacity to arrest acute flairs.

Further, patients suffering from mental illness who have difficulty with compliance of medication may benefit from epidural injection of relevant medication due to increased potency of spinal administration. Epidural injection also minimizes systemic side effects. Particularly in severe, acute cases, various psychotropic agents at oral doses can have undesirable side effects, such as extrapyramidal features, which lower compliance. Spinal administration can minimize systemic side effects of agents such as lithium, thorazine and haloperidol, as relative microdosing can be used to treat the symptoms.

Lastly, while the introduction of stem cells into the spinal canal can presently be performed, it requires surgery, which induces scar tissue and requires millions of cells to induce a graft. Spinal administration would be less invasive, could increase specificity of update into ischemic regions of the spinal cord, and therefore, could be more effective and have fewer risks. With a complete cord injury, introduction of stem cells below the level of spinal cord injury via the radicular artery carries little risk since trauma at the more proximal level has already occurred. The artery of Adamkiewicz is a narrow 1.2 mm diameter target, but affords direct vascular access to the spinal cord. The S1 vertebral foramen, at 21.3% and existing bilaterally, has nearly double the rate of incidental vascular penetration as other areas in lumbar spine. In one embodiment, a needle and stylet, or micro catheter with obturator, can identify a radicular artery and increase the probability of vascular penetration. Using the disclosed technology, as well as a Doppler ultrasound test, a practitioner can consistently reach this or another arterial target to deliver steroids, stem cells, or micro concentration of analgesics or medications. With a minimal diameter of 230 microns, the anterior spinal artery offers sufficient diameter to accommodate direct vascular injection, which, as described above, can increase specificity of uptake into ischemic regions of the spinal cord.

Needles and stylets, and catheters with obturators, that can detect biological substances, including nervous tissue and arterial circulation, could facilitate intentional radicular arterial access, allowing the interventionalist to place steroid, stem cells, medications, nano probes or other analgesic agents directly into the spinal circulation. This is dependent upon the interventionalist, or machine, being able to directly deliver the substance to the spinal circulation at the level of injury. The capacity of the device to detect nervous structures and vascular structures facilitates spinal vascular access. For more conventional procedures, simple detection of the vascular structure eliminates unintended vascular administration of medication, reducing the probability of catastrophic side effects.

The disclosed technology can reduce catastrophic complications associated with spinal procedures, reduce the severity of spinal cord injury associated with spinal procedures, offer new treatments for degenerative CNS conditions such as Multiple Sclerosis, and increase analgesic effect. Additionally, this alert system may enable mechanized surgical systems to accurately perform spinal procedures.

What is claimed is:

1. A biomarker detector system, comprising:
a light source; and
a medical instrument, including:
a needle having a first end and a second end;
a stylet having a first end and a second end;
a coating on the first end of the needle or the first end of the stylet of the medical instrument,
wherein the biomarker detector is configured to detect at least one biological substance; and
wherein the biological substance reacts to light from the light source;
an indication system located on the second end of the needle and the second end of the stylet,
wherein the indication system indicates the presence of the biological substance
by detecting the wavelength of the light as it bounces off of the biological substance at the coated end of the needle and the stylet.

2. The biomarker detector of claim 1, wherein the coating is located on the stylet, and wherein the indication system is located on a second end of the stylet and is visible to a user of the biomarker detector when the medical instrument is inserted into a patient.

3. The biomarker detector of claim 2, wherein the coating is limited to a portion of a first end of the stylet.

4. The biomarker detector of claim 1, wherein the coating is located on a first end of the needle, and wherein the indication system is located on a second end of the needle.

5. The biomarker detector of claim 1, wherein at least part of the indication system is located on a secondary piece of equipment.

6. The biomarker detector of claim 1, wherein the indication system visually indicates the presence of the at least one biological substance.

7. The biomarker detector of claim 1, wherein the indication system audibly indicates the presence of the at least one biological substance.

8. The biomarker detector of claim 1, wherein the indication system indicates the type of biological substance the detector has detected.

9. A biomarker detector system, comprising:
a light source; and
a medical instrument, including:
a needle having a first end and a second end; and
a stylet;
a coating located on the first end of the needle,
wherein the biomarker detector is configured to detect at least one biological substance; and
wherein the biological substance reacts to light from the light source;
an indication system located on the second end of the needle, wherein the indication system indicates the presence of
the biological substance
by detecting the wavelength of the light as it bounces off the biological substance at the coated end of the needle.

* * * * *